United States Patent
Becker

(10) Patent No.: US 7,169,163 B2
(45) Date of Patent: *Jan. 30, 2007

(54) TRANSNASAL METHOD AND CATHETER FOR LACRIMAL SYSTEM

(76) Inventor: Bruce Becker, 6187 Coral Pink Cir., Woodland Hills, CA (US) 91367

(*) Notice: Subject to any disclaimer, the term of this patent is extended or adjusted under 35 U.S.C. 154(b) by 317 days.

This patent is subject to a terminal disclaimer.

(21) Appl. No.: 10/259,630

(22) Filed: Sep. 30, 2002

(65) Prior Publication Data

US 2004/0064083 A1 Apr. 1, 2004

(51) Int. Cl.
*A61M 29/00* (2006.01)

(52) U.S. Cl. .................. 606/196; 606/191; 606/192

(58) Field of Classification Search ............... 606/191, 606/192, 194, 196, 198, 199; 604/103.07, 604/98.02
See application file for complete search history.

(56) References Cited

U.S. PATENT DOCUMENTS

| | | | | |
|---|---|---|---|---|
| 3,889,685 A | * | 6/1975 | Miller et al. ................. 604/8 |
| 4,323,071 A | * | 4/1982 | Simpson et al. ............. 606/194 |
| 4,380,237 A | * | 4/1983 | Newbower ................... 600/506 |
| 4,437,856 A | * | 3/1984 | Valli ............................ 604/29 |
| 4,459,977 A | * | 7/1984 | Pizon et al. .................. 600/17 |
| 4,771,776 A | * | 9/1988 | Powell et al. ............... 128/344 |
| 4,777,951 A | * | 10/1988 | Cribier et al. .............. 128/344 |
| 4,943,275 A | * | 7/1990 | Stricker ....................... 600/18 |
| 4,946,440 A | * | 8/1990 | Hall ............................ 604/95 |
| 5,021,043 A | | 6/1991 | Becker et al. |
| 5,021,045 A | * | 6/1991 | Buckberg et al. ............ 604/53 |
| 5,169,386 A | | 12/1992 | Becker et al. |
| 5,228,441 A | * | 7/1993 | Lundquist ................... 600/380 |
| 5,338,295 A | * | 8/1994 | Cornelius et al. ............ 604/96 |
| 5,425,708 A | * | 6/1995 | Nasu ....................... 604/102.03 |
| 5,928,192 A | * | 7/1999 | Maahs ..................... 604/96.01 |
| 5,974,343 A | * | 10/1999 | Brevard et al. ............ 607/102 |
| 6,083,188 A | * | 7/2000 | Becker ......................... 604/8 |
| 6,113,567 A | * | 9/2000 | Becker ......................... 604/8 |
| 6,238,364 B1 | * | 5/2001 | Becker ......................... 604/8 |
| 6,248,121 B1 | * | 6/2001 | Nobles ........................ 606/194 |
| 6,520,977 B2 | * | 2/2003 | Piraka ........................ 606/193 |

* cited by examiner

Primary Examiner—Michael J. Hayes
Assistant Examiner—Michael Mendoza
(74) Attorney, Agent, or Firm—Charmasson, Buchaca & Leach, LLP

(57) ABSTRACT

A balloon catheter for treatment of a patient's lacrimal system is applied transnasally without the use of a guide wire or a curve retention member. The catheter uses a stainless steel hypotube of sufficient stiffness and column strength to be pushed from the patent's nasal cavity through an opening-formed through the lateral nasal wall and lacrimal fossa, into the lacrimal sac. The catheter has an inflatable member mounted about a rigid bent distal segment. The opening is first formed by pushing small holes through the medial sac, lacrimal fossa, and lateral nasal wall with an instrument and coalescing the holes. The catheter is then introduced into the nasal cavity and pushed laterally through the opening by manipulating its proximal end. Pressurized fluid is then applied to the catheter to inflate the inflatable member and dilate the opening.

17 Claims, 5 Drawing Sheets

TRANSNASAL METHOD AND CATHETER FOR LACRIMAL SYSTEM

FIELD OF THE INVENTION

This invention relates to a method and catheter for treating the lacrimal system and, more particularly, to a transnasal method of treating the lacrimal system and a balloon catheter used in this method.

BACKGROUND AND DESCRIPTION OF THE PRIOR ART

To fully understand the invention, it is necessary to consider the anatomy and physiology of the lacrimal system. The orbital portion of the lacrimal gland is located in the superotemporal orbit and produces the aqueous layer of the tear film. Ductules from the orbital portion of the lacrimal gland pass through the adjacent palpebral lacrimal gland to empty in the superior conjunctival cul-de-sac. Smaller accessory lacrimal glands in the upper and lower lids also contribute to tear production The tears bathe the surface of the eye and then drain into the puncta and canaliculi in the medial upper and lower lids. The tears flow from the canaliculi into the lacrimal sac down the nasolacrimal duct into the nose.

The nasolacrimal duct can become obstructed on either a congenital or acquired basis When the nasolacrimal duct becomes obstructed, tears can no longer drain from the surface of the eye through the lacrimal system into the nose. The tears well up over the eye and spill over the lids onto the face. The patient has to constantly dab the eye with a tissue. In addition, tears stagnate in the lacrimal sac, bacteria multiply, and in many cases the lacrimal sac becomes infected (dacryocystitis). Dacryocystitis causes the lacrimal sac to become swollen, red and painful. Pus exudes from the sac and constantly covers the eye. In time, the dacryocystitis does not respond to antibiotics and surgery becomes necessary. At present, there is no medical therapy for acquired nasolacrimal duct obstruction other than antibiotics to temporarily suppress infection.

The condition can, however, be corrected surgically. Dacryocystorhinostomy (DCR) is the surgery required to correct nasolacrimal duct obstruction. In a DCR, a new opening (ostium) is created between the lacrimal sac and the nose. This allows tears to flow from the lacrimal sac through the DCR ostium into the nose. An external or incisional DCR required an incision on the side of the nose. In an open DCR, the surgeon creates a large 17 mm plus diameter opening in the bone and nasal muscosa. This procedure has significant morbidity, a prolonged recovery, and the threat of scarring and hemorrhage. In contrast, an endoscopic DCR has much less morbidity, no incision, and a quick recovery time. An endoscopic DCR may be performed using a balloon catheter, a laser, or traditional surgical instruments. A laser endoscopic DCR requires expensive and time-consuming lasers, and has a low success rate. An endoscopic DCR with traditional instruments places the eye and surrounding structures at risk because tissue is removed from the lacrimal sac and lateral nasal wall, with the instruments in the nasal cavity going toward the eye and orbit. Bleeding and edema may make it difficult to identify the relevant structures.

It has been found that a balloon catheter DCR is a much safer and cheaper form of DCR than a laser or an endoscopic DCR with traditional surgical instruments. The balloon catheter is positioned so that it extends from the lacrimal sac through the ostium and extends into the nose. Since the balloon DCR ostium is created by dilatation, rather than by excision or laser energy, there is no threat to the surrounding ocular and orbital structures, and there is less tissue trauma.

As shown in U.S. Pat. Nos. 5,021,043 and 5,169,043, I have previously co-invented balloon catheters for use in the lacrimal system. These balloon catheters are inserted from the eye through the small diameter (about 0.5 mm) delicate punctum and canaliculus into the lacrimal sac extending through the planned ostium into the nose. The deflated profile diameter of the balloon catheter must be very small in order to be pushed through, and avoid damage to, the small diameter and delicate canaliculus. The need for such a small deflated diameter limits the inflated diameter of the balloon to 5 mm. However, a 5 mm diameter ostium is much smaller than the 17 mm plus diameter ostium of an external DCR and leads to a higher stenosis rate of the balloon DCR ostium after surgery. A larger diameter balloon would create a larger-diameter ostium and lead to a higher surgical success rate.

This led to the concept disclosed beginning at column 7, line 29, and FIG. 4 of the U.S. Pat. No. 5,021,043 patent and beginning at column 8, line 34, and FIG. 4 of the U.S. Pat. No. 5,169,386 patent that a dilation catheter be introduced transnasally when a larger-diameter balloon is required. However, as taught in these patents, the dilation catheter is inserted over a guide wire. Although this technique is useful, it involves a number of time-consuming steps, including the insertion of a guide wire through the lacrimal system, and then separately advancing the balloon catheter over the guide wire. This technique requires the placement of a guide wire through the canaliculi into the nose. The surgeon then reaches up the nose with a hemostat or other instrument to grasp the guide wire and pull it out of the external naris of the nose. A flexible balloon catheter is then passed up the nose over the guide wire and through the lateral nasal wall into the lacrimal sac, or up the nasolacrimal duct into the lacrimal sac. However, there are problems with this method. First, there may be difficulty locating and grasping the guide wire in the nose, especially if even mild bleeding is present. The guide wire may pass posteriorly into the throat (pharynx) rather than in the direction of the external naris. There is often resistance to pulling the balloon from the nasal cavity into the lacrimal sac and considerable force is required to pull the balloon and guide wire into the lacrimal sac. This pull on the guide wire can cause it to slice through the delicate canaliculi, which may lead to secondary fibrosis and obstruction of the canaliculi after surgery.

The U.S. Pat. No. 5,169,386 patent also discloses an alternative dilation catheter, which does not use a guide wire, but there is no suggestion that this catheter be inserted transnasally. The catheter is constructed to simulate a standard ophthalmic probe in stiffness, in terms of both column strength and resistance to lateral bending, with sufficient flexibility to enable it to conform to the contours of the lacrimal system. The catheter, as provided, is initially straight, but the catheter may be bent between 0°–30° to simulate the curvature of an ophthalmic probe. A curve retention element is inserted in the catheter to retain the curved shape and to increase the columnar and flexural stiffness of the distal portion of the catheter to enhance its ability to be forced through a constricted portion of the lacrimal system. The catheter is formed of a stainless steel hypotube having an outer diameter of 0.022" and an inner diameter of 0.017".

This catheter is not suitable for transnasal insertion. The tube does not have sufficient stiffness and column strength to enable the deflated balloon catheter to be pushed from the nasal cavity through a small, tight opening in the lateral nasal wall and lacrimal fossa into the lacrimal sac. Moreover, the bent distal portion is not angled to a degree necessary for ready insertion through the opening.

SUMMARY OF THE INVENTION

A balloon catheter of the invention can be introduced transnasally into the area of a planned DCR ostium. The catheter has a larger deflated profile and, thus, a larger inflated diameter, than a balloon catheter introduced through the delicate canaliculi. The balloon catheter of the invention does not need a guide wire; and, therefore, there is no chance that a guide wire will damage the delicate canaliculi. A larger diameter balloon DCR ostium is less likely to stenose after surgery and results in a better surgical success rate.

The balloon catheter of the invention comprises a hypotube formed of stainless steel of sufficient stiffness and column strength to enable the deflated balloon catheter to be pushed from the nasal cavity through a prepared small, tight opening in the lateral nasal wall and lacrimal fossa into the lacrimal sac. A distal end segment of the hypotube has a rounded bend, placing the distal segment at an angle of 70° to 115°, preferably 90°, to a long proximal segment or shaft. This bend allows the surgeon to rotate or shift the position of the long proximal catheter shaft, thus placing the distal balloon catheter segment in position to enter from the nasal cavity into the lacrimal sac at various angles appropriate to each individual patient. Due to the stiffness and strength of the hypotube, neither a guide wire nor a curve retention element are necessary.

The distal segment of the balloon catheter from the outside of the bend to the end of the catheter is 14 mm which is short enough to allow it to be rotated within the nasal cavity and long enough to allow a balloon of sufficient length and diameter to be attached to the hypotube for dilatation of the balloon DCR ostium.

The balloon is formed of inflatable material with a first neck bonded with adhesive to the very distal portion of the distal segment of the hypotube and a second neck bonded with adhesive to the distal end of the proximal shaft, the bend, and the proximal end of the distal segment. This permits a longer working segment of balloon to be used, because the area of adhesion of the balloon includes the bend and the adjacent portion of the proximal long segment of the hypotube. The proximal end of the catheter tube has a luer lock with wings or an expansion to allow the catheter to be attached to tubing from the inflation device. The wings or expansion allow the surgeon to more easily hold, manipulate, and push the balloon catheter.

According to the method of the invention, a very large ostium is formed between the lacrimal sac and the nasal cavity with the use of a very large balloon inserted transnasally. The balloon is deflated to allow the catheter, which is of sufficient stiffness, to be pushed through the prepared opening formed from the nasal cavity through the lateral nasal wall and lacrimal fossa into the lacrimal sac The balloon is then inflated to enlarge the opening and create the very large ostium. The balloon catheter is inserted without the use of a guide wire.

The portion of the distal end after the bend is sufficiently short to enable the catheter to be positioned in the nasal cavity to bring the distal end to the level of the prepared opening. The catheter is then rotated or shifted to align the distal end with the prepared opening, as required by the anatomy of the individual patient. The distal end is then pushed through the prepared opening to position the deflated balloon in the opening. The balloon is then inflated to enlarge the opening to the outer diameter of the inflated balloon, thus forming the very large ostium.

Since the method of the insertion requires insertion of the balloon catheter transnasally, the trauma associated with insertion through the delicate canaliculi is avoided. The catheter and method of the invention provide a satisfactory endoscopic DCR and thus avoid the trauma associated with an external (incisional) DCR. The catheter and method of the invention achieve a high surgical success rate.

DETAILED DESCRIPTION

Figure 1:
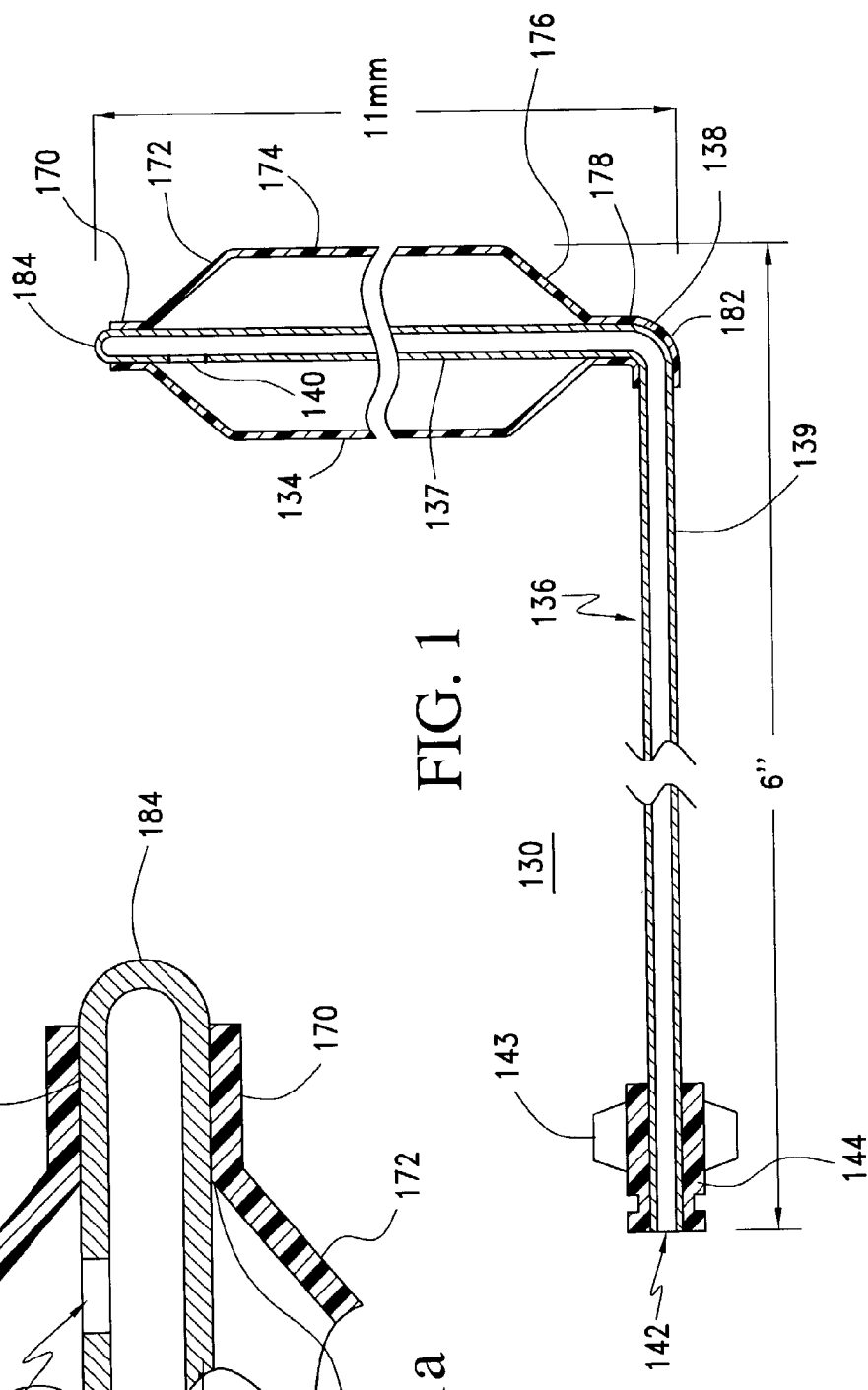
FIG. 1 is a schematic drawing of a preferred embodiment of a lacrimal balloon catheter of the invention.
Figure 1A:
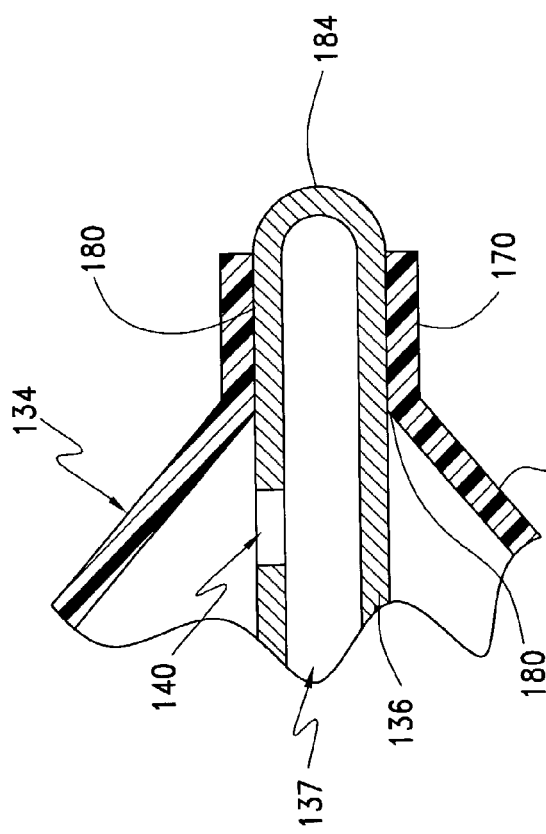
FIG. 1a is a close-up schematic drawing of the tip of the distal segment of the balloon catheter of FIG. 1.
Figure 7:
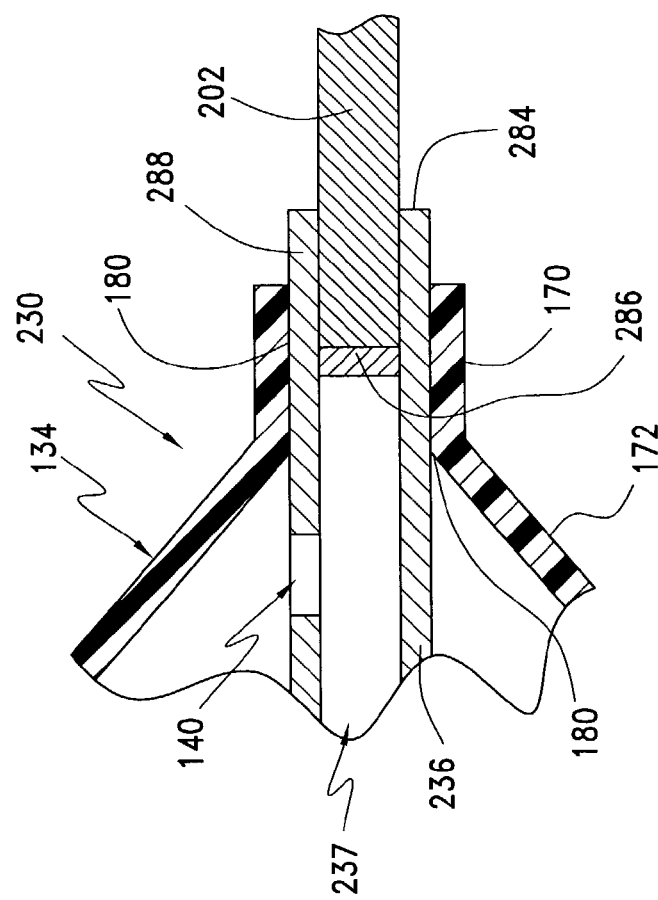
FIG. 7 is a schematic diagram showing a method step of an alternative embodiment of the method of the invention.
Figure 6:
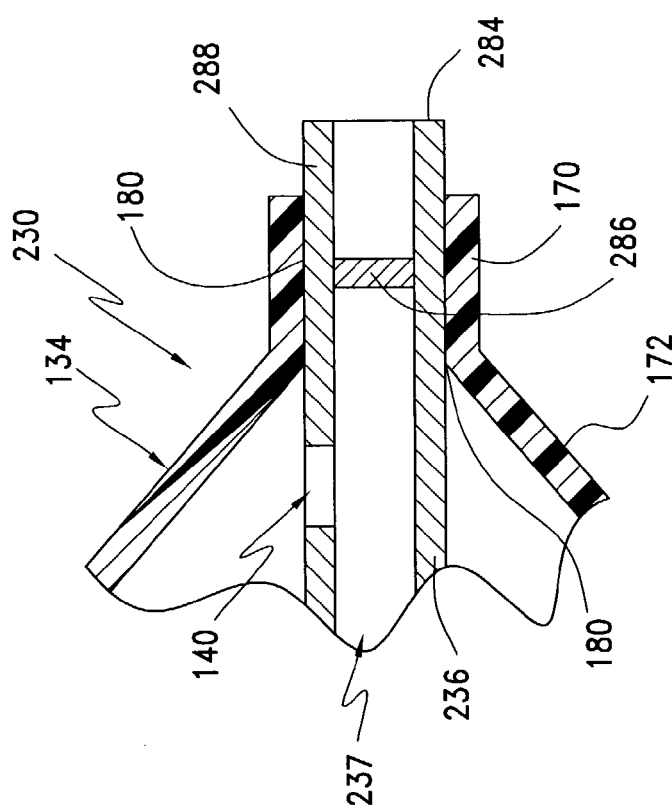
FIG. 6 is a close-up schematic drawing of the tip of the distal portion of an alternative embodiment of a balloon catheter of the invention.

As shown in FIGS. 1 and 1a, a balloon catheter 130 of the invention is assembled from a tube 136, preferably a stainless steel hard tempered hypotube which has a circular bend 138 of 0.13" radius such that distal segment 137 is oriented 70° to 115°, preferably 90°, to proximal segment 139. The distance from the distal tip 184 of distal segment 137 to the outer wall of proximal segment 139 of hypotube 136 is 4 mm to 30 mm, preferably 14 mm, as shown in FIG. 1. The distal tip 184 of the hypotube 136 is closed, whereas the proximal end 142 is open. However, the lumen of tube 136 may be closed in the distal segment 137, up to 10 mm from the distal tip 184 allowing the distal tip 184 to remain open for engagement with a probe, as shown in FIGS. 6 and 7. The proximal end 142 of hypotube 136 is inserted into a mold for forming luer 144. Heated plastic is injected into the mold to form luer 144 attached to proximal end 142. The inner diameter of the luer 144 matches the external diameter of the hypotube 136. The luer 144 has wings 143 or other enlargement or expansion on it to enable the surgeon to better hold and manipulate the balloon catheter 130. Catheter 130 is 4" to 10" long, preferable 6" in length as measured from proximal end 142 to distal tip 184, as shown in FIG. 1. The wall of tube 136 should be of such thickness that the tube has sufficient stiffness and column strength that distal segment 137 of a deflated catheter can be pushed through a prepared small, tight opening in the patient's lateral nasal wall. This may require considerable pressure in some cases. It has been found that a tube with a wall thickness of at least 0.035" will be satisfactory. A preferred tube has an outer diameter of 0.083" and an inner diameter of 0.039" with a wall thickness of 0.044".

The catheter 130 has a port 140 in the distal segment 137, which is formed by inserting temporarily a discardable wire segment into the tube 136. This is done before inserting hypotube 136 into luer 144. A transverse slot is cut in the tube 136 approximately 2 mm to 14 mm, preferably 4 mm, from its distal end 184 to form port 40. The slot extends in depth to approximately one third of the diameter of tube 136. A wire wheel is used to remove any burrs, and the discardable core wire is removed and discarded.

Catheter 130 has sufficient column strength and resistance to lateral bending (stiffness) to enable the deflated catheter to be pushed through the initial prepared opening in the lateral nasal wall and lacrimal fossa into the lacrimal sac. This may require considerable pressure in some cases.

A balloon 134 is preferably formed of polyethylene terephthalate and has a length of approximately 4 mm to 30 mm, preferably 14 mm, and a working inflated diameter of 2 mm to 14 mm, preferably 9 mm, for use in the lacrimal system. The balloon has a distal neck 170, a distal tapered region 172, a center region 174, a proximal tapered region 176, and a proximal neck 178. During installation, tube 136 is cleaned with isopropanol and then coated with a primer, "Loctite 770." The balloon is placed over the distal end of tube 136 to align the distal end of distal neck 170 with distal end 184 of tube 136. An adhesive, such as cyanoacrylate, is used. An acceptable adhesive "Loctite 4081" is available from Loctite Corporation. The adhesive is applied to distal end of distal neck 170 and the proximal end of proximal neck 178 to form bonds 180 and 182, respectively. The adhesive is applied to the balloon necks 170, 178 using a small mandrel such as a wire approximately 0.010" to 0.014" in diameter. The adhesive wicks into the necks due to capillary action. Proximal neck 178 and proximal tapered region 176 may be bonded on distal segment 137 of tube 136 or extend over bend 138 onto the distal end portion of proximal segment 139 of tube 136. Extension of the proximal neck 178 onto bend 138 and proximal segment 139 allows a greater length of the working diameter, i.e., center region 174, to be on distal segment 137 of tube 136.

Figure 2:
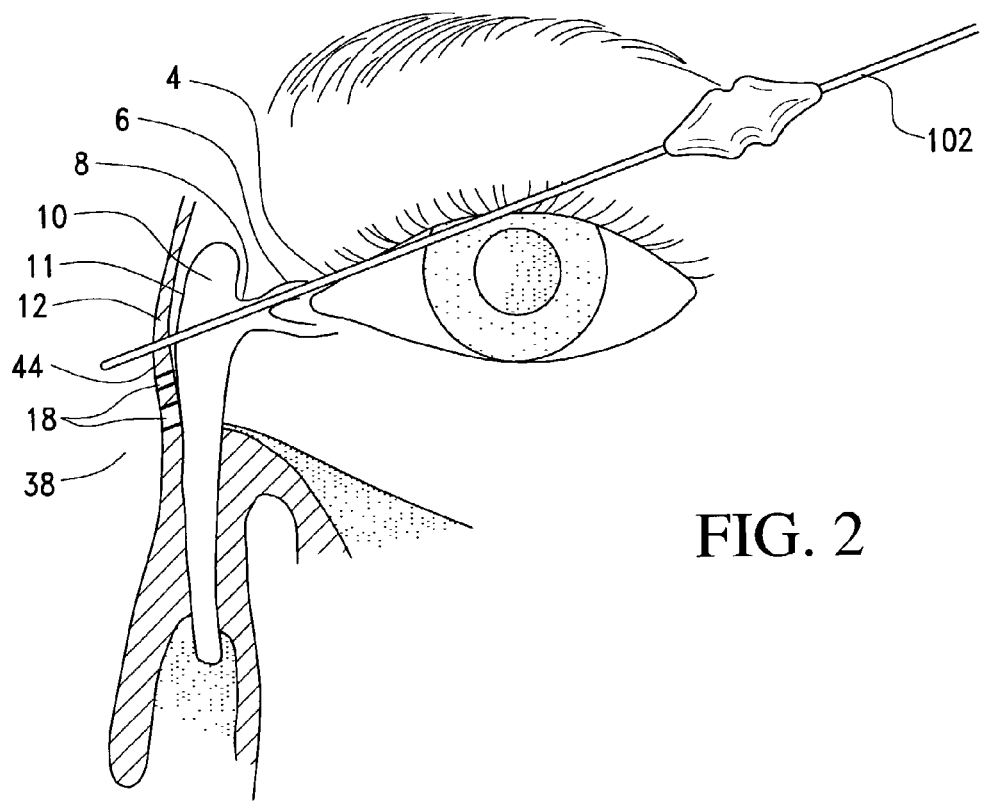
FIG. 2 is a schematic drawing of a step of the method of the invention showing a patient with an obstructed nasolacrimal duct in which a metal probe has been passed through the punctum, canaliculus, lacrimal sac, and multiple spots in the lacrimal fossa and lateral nasal wall into the nose.
Figure 3:
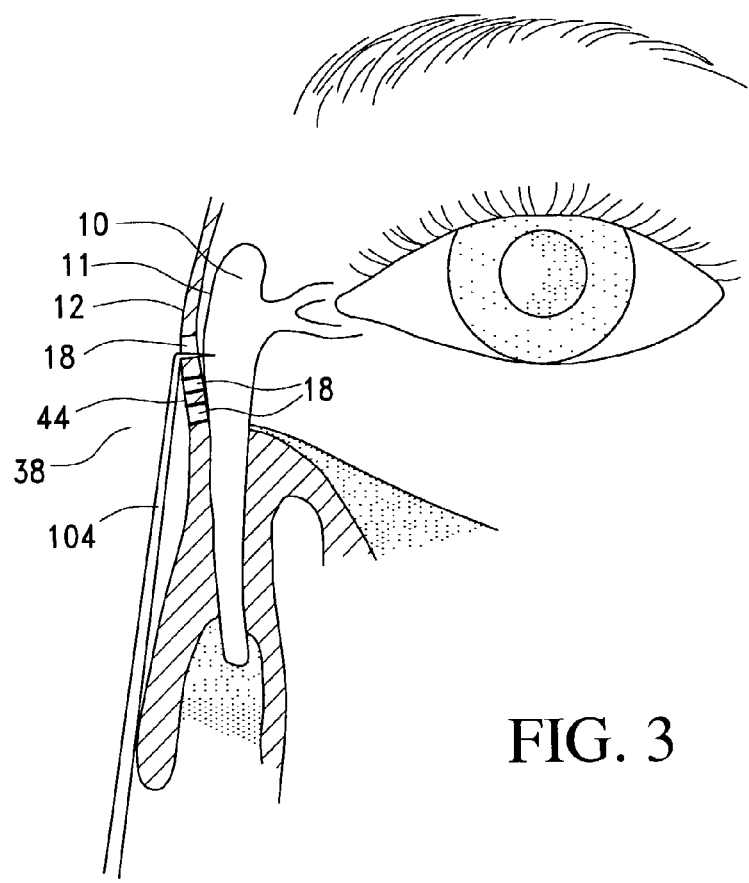
FIG. 3 is a schematic drawing showing another step of the method of the invention in which a nerve hook brought up the nasal cavity, pushed into the small openings in the lateral nasal wall and lacrimal fossa, and moved to coalesce these small openings into a larger opening.

A first step of the method of the invention is shown in FIG. 2. A Bowman probe 102 is brought through superior punctum 4 of the patient's eye, superior canaliculus 6, common canaliculus 8, and lacrimal sac 10, and then pushed through the medial sac wall 11, lacrimal fossa bone 12, and lateral nasal wall 44 into the nasal cavity 38. Probe 102 is pulled back into lacrimal sac 10, and pushed through four or fives areas of medial sac wall 11, lacrimal fossa bone 12, and lateral nasal wall 44 into nasal cavity 38. The multiple openings 18 in the medial sac wall 11, lacrimal fossa 12, and lateral nasal wall 44 are coalesced into one prepared opening 19 (FIG. 4) by moving probe 102 in a see-saw fashion or by bringing a nerve hook 104 into nasal cavity 38, and pushing it into openings 18 and dragging nerve hook 104 across multiple openings, as shown in FIG. 3.

Figure 4:
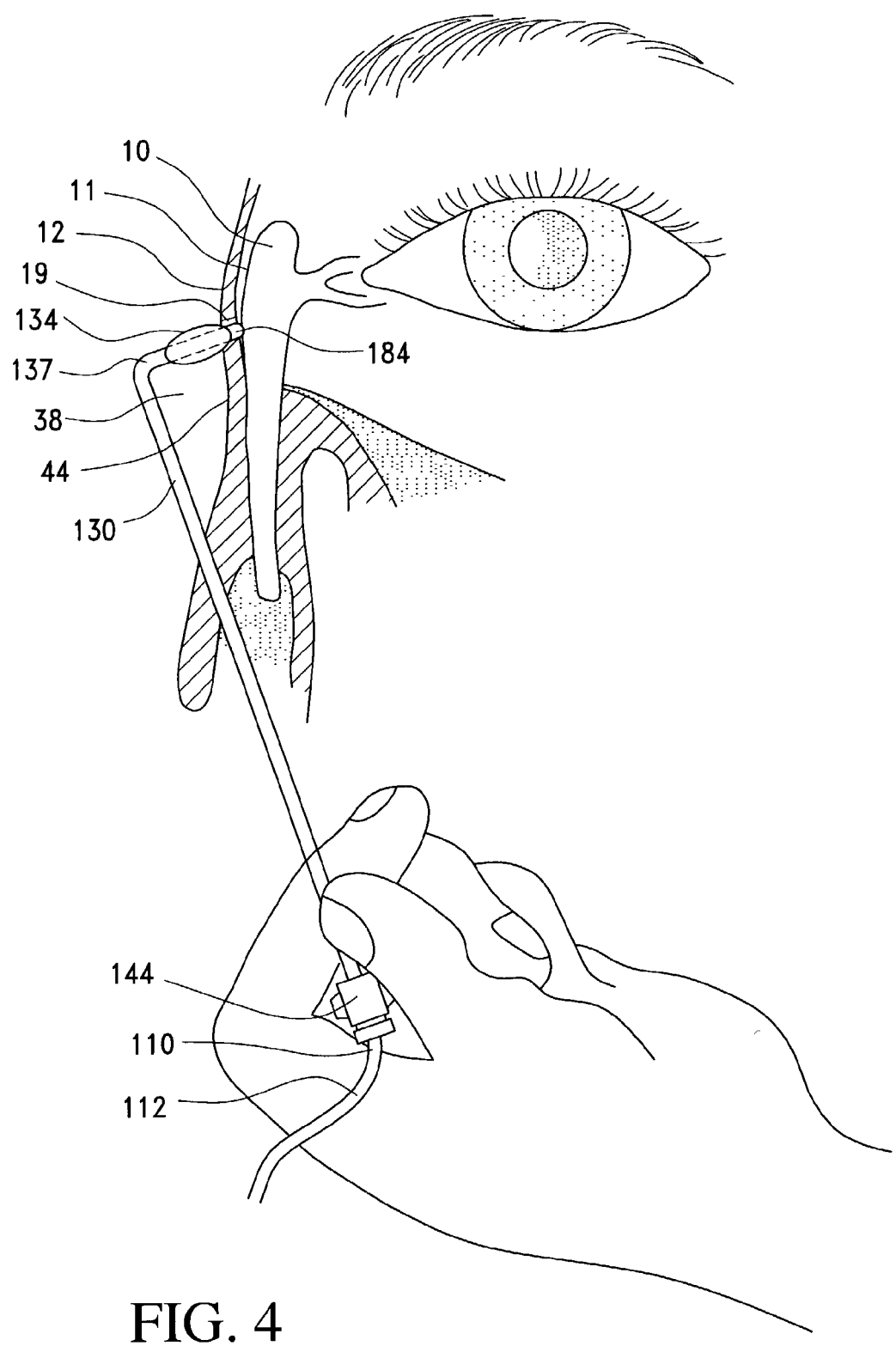
FIG. 4 is a schematic drawing showing a further step of the method of the invention in which a deflated balloon catheter of the invention, which has been brought into the nasal cavity and pushed through the small opening in the lateral nasal wall and lacrimal fossa into the lacrimal sac.

Turning to FIG. 4, the deflated transnasal lacrimal balloon catheter 130 is then brought into nasal cavity 38, and distal segment 137 is pushed through prepared opening 19 created by coalescing smaller openings 18 in lateral nasal wall 44, lacrimal fossa 12, and medial wall 11 of lacrimal sac 10, such that distal end 184 of distal segment 137 of balloon catheter 130 extends into lacrimal sac 10.

Figure 5:
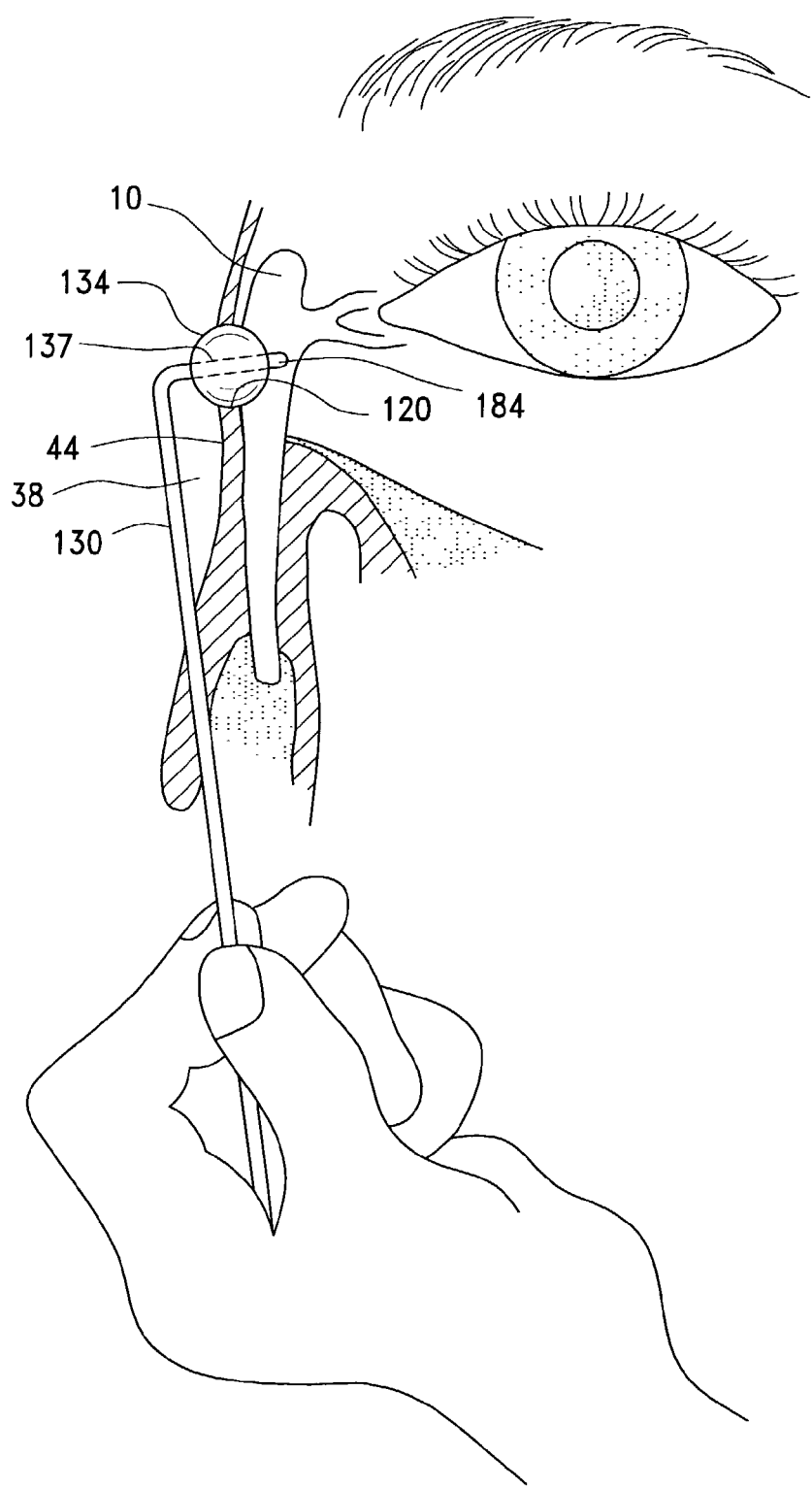
FIG. 5 is a schematic drawing showing a step of the method of the invention in which the balloon catheter with the balloon inflated is within the ostium and lacrimal sac.

The luer lock 144 on proximal end 142 of balloon catheter 130 connects to the distal end 110 of tube 112 of the inflation device, which supplies fluid under pressure. As seen in FIG. 5, balloon 134 is inflated to 9 bars for 20 seconds to expand opening 19 to form ostium 120 then deflated. Distal segment 137 is then slightly repositioned to insure thorough dilation and inflated again to 9 bars for 20 seconds. Balloon 134 is then deflated and withdrawn from nasal cavity 38, leaving a large ostium 120 formed between lacrimal sac 10 and nasal cavity 38.

An alternative embodiment of the balloon catheter of the invention is shown in FIG. 6. In this embodiment, the catheter 230 has a distal segment 237, which are identical to catheter 130 and segment 137, as shown in FIG. 1, except for the point of closure of tube 136. Whereas, as described above, distal segment 137 in FIG. 1 is closed at its distal end 184, in the embodiment of FIG. 6, tube 236, and distal segment 237 are closed by closure wall 286 that is located between slot 140 and the distal end 284. Since distal segment 237 is closed after slot 140, fluid will still flow through slot 140 to inflate balloon 134 when air under pressure is applied to tube 236. However, there will now be an open-ended tube segment 288 between closure wall 286 and distal end 284.

As shown in FIG. 7, this open-ended tube segment 288 may be used to receive an end of a probe 202, provided that the outer diameter of probe 202 is slightly smaller than the inner diameter of tube segment 288. Such a probe engaged with open-ended tube segment 288 can be useful for moving distal end 284 to a proper position for engagement with an opening 19 which is to be enlarged by inflating balloon 134, as described above.

It should be understood that the foregoing description of the invention is intended merely to be illustrative and other modifications, embodiments, and equivalents may be apparent to those skilled in the art without departing from the spirit and scope of the invention.

The invention claimed is:

1. A balloon catheter for dilating a prepared small, tight nasal opening in a wall separating a patient's lacrimal sac and the patient's nasal cavity, comprising a tubular catheter body having a proximal end, a proximal segment, a distal end, and a distal segment; an inflatable member disposed about said distal segment, said distal segment having a slot; said catheter body being closed at a point that is closer to said distal end that is said slot; means for applying fluid under pressure to said proximal end of said catheter body, said fluid under pressure flowing through said slot to inflate said inflatable member for dilating said prepared opening; and said catheter body being formed of a hypotube of sufficient stiffness and column strength to enable said catheter, when said inflatable member is deflated, to be pushed from said nasal cavity through said prepared opening in said lateral nasal wall into said lacrimal sac in the absence of a guide wire or curve retention element;

wherein said catheter body is formed of stainless steel and, said catheter body has an outer diameter of 0.083" and an inner diameter of 0.039" with a wall thickness of 0.044".

2. A balloon catheter for dilating a prepared small, tight nasal opening in a wall separating a patient's lacrimal sac and the patient's nasal cavity, comprising a tubular catheter body having a proximal end, a proximal segment, a distal end, and a distal segment; an inflatable member disposed about said distal segment, said distal segment having a slot; said catheter body being closed at a point that is closer to said distal end that is said slot; means for applying fluid under pressure to said proximal end of said catheter body, said fluid under pressure flowing through said slot to inflate said inflatable member for dilating said prepared opening; and said catheter body being formed of a hypotube of sufficient stiffness and column strength to enable said catheter, when said inflatable member is deflated, to be pushed from said nasal cavity through said prepared opening in said lateral nasal wall into said lacrimal sac; and, wherein said catheter body is closed at a point spaced from said distal end and between said slot and said distal end, whereby an open-ended distal portion of said distal segment is provided, said open-ended distal portion being engagable by an end of a probe to help guide said catheter body.

3. A balloon catheter for dilating a prepared opening in a lateral nasal wall separating a patient's lacrimal sac and the patient's nasal cavity, consisting essentially of: a tubular catheter body having a proximal end, a proximal segment, a distal end, and a distal segment; an inflatable member disposed about said distal segment, said distal segment having a slot; said catheter body being closed at a point that is closer to said distal end than is said slot; means for applying fluid under pressure to said proximal end of said catheter body, said fluid under pressure flowing through said slot to inflate said inflatable member for dilating said prepared opening; and said distal segment having a rigid, rounded bend placing said distal segment at an angle of 70° to 115° to said proximal segment;

wherein said inflatable member comprises a distal neck, a center region, and a proximal neck and said proximal neck is adhesively bonded to the proximal end of said distal segment and said bend, said distal neck is adhesively bonded to the portion of said distal segment between said slot and said distal end, thereby allowing a greater length of said center region to be on said distal segment.

4. A balloon catheter for dilating a prepared opening in a lateral nasal wall separating a patient's lacrimal sac and the patient's nasal cavity, consisting essentially of: a tubular catheter body having a proximal end, a proximal segment, a distal end, and a distal segment; an inflatable member disposed about said distal segment, said distal segment having a slot; said catheter body being closed at a point that is closer to said distal end than is said slot; means for applying fluid under pressure to said proximal end of said catheter body, said fluid under pressure flowing through said slot to inflate said inflatable member for dilating said prepared opening; and said distal segment having a rigid, rounded bend placing said distal segment at an angle of 70° to 115° to said proximal segment;

wherein said inflatable member comprises a distal neck, a center region, and a proximal neck and said proximal neck is adhesively bonded to the proximal end of said distal segment, the distal end of said proximal segment, and said bend, said distal neck is adhesively bonded to the portion of said distal segment between said slot and said distal end, thereby allowing a greater length of said center region to be on said distal segment.

5. A method forming a relatively large opening in a lateral nasal wall separating a patient's lacrimal sac and nasal cavity, comprising: providing a balloon catheter having a rigid tubular catheter body formed with a proximal segment, a bend, and a distal segment at an angle of 70° to 115° with said proximal segment, an inflatable member mounted around said distal segment, a slot through a wall of said distal segment within said inflatable member, said tubular catheter body being closed at a point distally of said slot, and means for providing fluid under pressure at the proximal end of said tubular catheter body to inflate said inflatable member; forming a small, tight prepared opening through the patient's medial sac wall and lacrimal fossa, and said lateral nasal wall with one or more surgical tools, said opening being of such size that it will snugly receive said distal segment with said inflatable member deflated; pushing said distal segment of said catheter body into said prepared opening with said inflatable member deflated without using a guide wire or curve retention element; and introducing said fluid under pressure through said proximal end of said catheter body and said slot to inflate said inflatable body and dilate said prepared opening.

6. The method of claim 5, further comprising deflating said inflatable body, slightly repositioning said distal segment and re-inflating said inflatable member to insure thorough dilation of said prepared opening.

7. The method of claim 5, wherein said inflatable member is inflated to nine bars for twenty seconds.

8. The method of claim 5, wherein said step of forming said prepared opening comprises bringing a Bowman probe through the patient's superior punctum, superior canaliculus, common canaliculus, and lacrimal sac and pushing said probe through the patient's medial sac wall, lacrimal fossa bone, and lateral nasal wall into the patient's nasal cavity to form a small opening.

9. A method forming a relatively large opening in a lateral nasal wall separating a patient's lacrimal sac and nasal cavity, comprising: providing a balloon catheter having a tubular catheter body formed with a proximal segment, a bend, and a distal segment at an angle of 70° to 115° with said proximal segment, an inflatable member mounted around said distal segment, a slot through a wall of said distal segment within said inflatable member, said tubular catheter body being closed at a point distally of said slot, and means for providing fluid under pressure at the proximal end of said tubular catheter body to inflate said inflatable member; forming a small, tight prepared opening through the patient's medial sac wall and lacrimal fossa, and said lateral nasal wall with one or more surgical tools, said opening being of such size that it will snugly receive said distal segment with said inflatable member deflated; pushing said distal segment of said catheter body into said prepared opening with said inflatable member deflated; and introducing said fluid under pressure through said proximal end of said catheter body and said slot to inflate said inflatable body and dilate said prepared opening;

wherein said step of forming said prepared opening comprises bringing a Bowman probe through the patient's superior punctum, superior canaliculus, common canaliculus, and lacrimal sac and pushing said probe through the patient's medial sac wall, lacrimal fossa bone, and lateral nasal wall into the patient's nasal cavity to form a small opening; and further comprising repeating said pushing of said probe to form several small openings through said medial sac wall, lacrimal fossa bone, and lateral nasal wall into said nasal cavity.

10. The method of claim 9, further comprising coalescing said several small openings to form said prepared openings by moving said probe in a see-saw fashion within said several openings.

11. The method of claim 9, further comprising coalescing said several small openings to form said prepared opening by bringing a nerve hook across said several small openings.

12. The method of claim 5, wherein said catheter body is formed of a hypotube of sufficient stiffness and column strength to enable said distal segment with said inflatable member deflated to be pushed through said prepared opening.

13. A method forming a relatively large opening in a lateral nasal wall separating a patient's lacrimal sac and nasal cavity, comprising: providing a balloon catheter having a tubular catheter body formed with a proximal segment, a bend, and a distal segment at an angle of 70° to 115° with said proximal segment, an inflatable member mounted around said distal segment, a slot through a wall of said distal segment within said inflatable member, said tubular catheter body being closed at a point distally of said slot, and means for providing fluid under pressure at the proximal end of said tubular catheter body to inflate said inflatable member; forming a small, tight prepared opening through the patient's medial sac wall and lacrimal fossa, and said lateral nasal wall with one or more surgical tools, said opening being of such size that it will snugly receive said distal segment with said inflatable member deflated; pushing said distal segment of said catheter body into said prepared opening with said inflatable member deflated; and introducing said fluid under pressure through said proximal end of said catheter body and said slot to inflate said inflatable body and dilate said prepared opening; and wherein said proximal segment is introduced into a patient's nasal cavity until said distal segment is moved to a point adjacent said prepared opening, and said proximal segment, is rotated to align said distal segment with said prepared opening to facilitate entry of said distal segment into said prepared opening.

14. The method of claim 5, wherein said tubular catheter body is closed at a point short of the distal end of said catheter body to provide an open-ended portion of said distal segment, and wherein said method further comprises inserting a probe into said open-ended portion to facilitate movement of said distal segment to a desired location.

15. A method forming a relatively large opening in a lateral nasal wall separating a patient's lacrimal sac and nasal cavity, comprising: providing a balloon catheter having a tubular catheter body formed with a proximal segment and a distal segment having a rigid, rounded bend, an inflatable member mounted around said distal segment, a slot through a wall of said distal segment within said inflatable member, said tubular catheter body being closed at a point distally of said slot, and means for providing fluid under pressure at the proximal end of said tubular catheter body to inflate said inflatable member, said catheter body being formed to have sufficient stiffness and column strength to enable said catheter, when said inflatable member is deflated, to be pushed from said nasal cavity through a small, tight prepared opening into said lacrimal sac without necessitating a guide wire or curve retention element; forming a prepared opening through said lateral nasal wall with one or more surgical tools, said opening being of such size that it will snugly receive said distal segment with said inflatable member deflated; pushing said distal segment of said catheter body into said prepared opening with said inflatable member deflated; and introducing said fluid under pressure through said proximal end of said catheter body and said slot to inflate said inflatable body and dilate said prepared opening.

16. The method of claim 15, further comprising deflating said inflatable body, slightly repositioning said distal segment and re-inflating said inflatable member to insure thorough dilation of said prepared opening.

17. A balloon catheter for dilating an opening between a patient's lacrimal sac and nasal cavity, said catheter consisting essentially of:

a rigid tubular catheter body having a proximal end, a proximal segment, a distal end, and a distal segment having a rigid, rounded bend;

an inflatable member disposed about said distal segment; and, means for successively inflating said member;

wherein said distal segment is at an angle of 70° to 115° to said proximal segment; and, wherein said catheter body is closed at a point spaced from said distal end, whereby an open-ended distal portion of said distal segment is provided, said open-ended distal portion being engagable by an end of a probe to help guide said catheter body.

* * * * *